United States Patent [19]

Parenti

[11] Patent Number: 5,260,462
[45] Date of Patent: Nov. 9, 1993

[54] PURIFICATION OF TAUROURSODESOXYCHOLIC ACID DIHYDRATE

[75] Inventor: Massimo Parenti, Novi Ligure, Italy

[73] Assignee: Prodotti Chimici E Alimentari S.P.A., Alessandria, Italy

[21] Appl. No.: 913,996

[22] Filed: Jul. 17, 1992

Related U.S. Application Data

[63] Continuation of Ser. No. 794,683, Nov. 19, 1991, abandoned, which is a continuation of Ser. No. 528,887, May 29, 1990, abandoned.

[30] Foreign Application Priority Data

May 30, 1989 [IT] Italy ............................... 20698 A/89

[51] Int. Cl.$^5$ ............................................... C07J 41/00
[52] U.S. Cl. ................................................... 552/550
[58] Field of Search .......................................... 552/550

[56] References Cited

U.S. PATENT DOCUMENTS 3,221,008 11/1985 Wolf et al. ..................... 552/549

FOREIGN PATENT DOCUMENTS 3736918 11/1989 Fed. Rep. of Germany.

OTHER PUBLICATIONS

Hofmann A. F, Acta. Chem. Scan 17 (1963) 173–186.
CA, 109:231362e (1988) No. 25.
Introduction to Modern Liquid Chromatography (2nd edition) by L. R. Synder & J. J. Kirkland pp. 445–449.

Primary Examiner—Mark L. Berch
Assistant Examiner—Pavanaram K. Sripada
Attorney, Agent, or Firm—Nixon & Vanderhye

[57] ABSTRACT

Process for purification of tauroursodesoxycholic acid dihydrate prepared through reaction between taurine and mixed anhydride of ursodesoxycholic acid with an alkylcholoroformate using ion exchange resins.

3 Claims, No Drawings

PURIFICATION OF TAUROURSODESOXYCHOLIC ACID DIHYDRATE

This is a continuation of application Ser. No. 07/794,683, filed Nov. 19, 1991, now abandoned, which is a continuation of Ser. No. 07/528,887, filed May 29, 1990, now abandoned.

The present invention relates to the preparation of tauroursodesoxycholic acid dihydrate and more particularly to a process for the purification of that acid as obtained in unpurified form from the reaction between taurine and the mixed anhydride of ursodesoxycholic acid.

BACKGROUND OF THE INVENTION

Tauroursodesoxycholic acid dihydrate is known to be useful in the treatment of biliary diseases (Italian Patent No. 1,197,330). The acid is prepared by reacting taurine in the form of an aqueous solution of an alkali metal salt thereof with the mixed anhydride of ursodesoxycholic acid. The latter acid is prepared by reacting ursodesoxycholic acid and an alkyl chloroformate, particularly methyl or ethyl chloroformate, in the presence of a tertiary base, such as triethylamine.

The preparation of tauroursodesoxycholic acid takes place in high yields and in an industrially advantageous manner, but the unpurified reaction product contains several by-products besides unreacted reactants (taurine and ursodesoxycholic acid) including, for example the tertiary amine, and chlorides originating from the hydrolysis of the unreacted alkylchloroformate. For therapeutic use of the compound, these impurities must be substantially removed, preferably without prejudicing the overall yield.

In the case of the sodium salt of conjugates with taurine and glycine of ketodesoxycholic acid (Hofmann A.F., Acta Chem. Scan. 17 (1963), 173-186), it is known to carry out the purification from the tertiary amine using a cationic resin. However, different steps and methods are foreseen for the removal of the other impurities (by-products and unreacted reactants), particularly steps involving solvent extractions and repeated crystallization.

In the case of tauroursodesoxycholic acid, the product of the conjugation is in fact the sodium salt of the acid. The free acid may be obtained from this according to standard methods of chemistry by adding a suitable acid, for example and preferably hydrochloric acid. Consequently salts, particularly chlorides, are still formed which are impurities and must be removed.

Even having recourse to subsequent crystallization, there remain in the product unacceptable amounts of impurities which, in view of the therapeutic use, make necessary further time-consuming and expensive purification steps. This is obviously disadvantageous for industrial scale production.

The present invention aims at solving the problem discussed above in an industrially acceptable and advantageous manner.

DESCRIPTION OF THE INVENTION

It has been now found surprisingly and is the object of the present invention that if the aqueous solution resulting from the reaction between the mixed anhydride of the ursodesoxycholic acid and the taurine is serially percolated through a first strong cation exchange resin and then through a second weak anionic exchange resin, the unpurified reaction product is substantially separated from the tertiary amine base and from the chlorides, whereby purification in known manner from unreacted taurine and from ursodesoxycholic acid is readily and easily carried out, leading to the taurousodesoxycholic acid dihydrate in pure form suitable for pharmaceutical use.

It has been particularly found, and this is one of the advantages of the present invention, that the passage through the first column can be carried out in a simple and safe manner since the raw reaction solution, containing the sodium salt of tauroursodesoxycholic acid, has a pH from neutral to weakly alkaline, whereas the free acid is a strong acid and the aqueous solution thereof has an acid pH (2-3). Consequently, by monitoring the eluate of the first column and particularly the pH thereof or a parameter related thereto, it is easy to determine the beginning and the end of the phase in which the acid can be released and consequently the eluate in which substantially pure acid passes (apart from the unreacted taurine and ursodesoxycholic acid), thereby obviating further time-consuming and complicated analyses.

Secondly, it is no longer necessary to add a mineral acid, particularly hydrochloric acid, to the raw reaction product to recover the free acid. In this way, not only are further impurities avoided, but also losses of the desired active principle, even modest reductions of yields, are avoided.

A further advantage, which is readily appreciated by referring for example to the above-mentioned paper by Hofmann, is the fact the purification is simple and reliable which, in the production of a therapeutically active principle, has remarkable importance.

The selection of the ion exchange resin shall not be difficult for the skilled man, provided that the cationic resin is strong in $H^+$ form and the anionic one is of weak type.

EXAMPLE OF THE INVENTION

The following example provides a non-limiting example of the purification process according to the invention.

EXAMPLE (a) Mixed anhydride of the ursodesoxycholic acid.

A solution of 48 g of ursodesoxycholic acid and 12.5 g of triethylamine in 300 ml of dioxane, cooled to $-5°$ C., is added with 13.4 g of ethylchloroformate.

The reaction is exothermic and the internal temperature of $-5°$ C. is maintained by external cooling using acetone and dry ice. When the addition is complete, the mixture is maintained under stirring for 15-30 minutes, leaving the suspension to heat up to room temperature.

The suspension is filtered from triethylamine hydrochloride and the filtered organic solution is used for the next reaction.

(b) Sodium salt of tauroursodesoxycholic acid.

A solution of 19.2 g of taurine in 120 ml of 1N sodium hydroxide is prepared. This solution is poured onto the solution of mixed anhydride prepared as described in (a) above. The reaction is stirred for 3 hours and after that time it is filtered to remove the unreacted taurine.

(c) Tauroursodesoxycholic acid Dihydrate.

The solution of sodium salt of the tauroursodesoxycholic acid prepared as described in (b) (500 ml) is percolated through a column packed with 100 ml of strong cationic resin, Relite CF, in ionic form H+. at a rate of 500 ml/hour.

The solution of tauroursodesoxycholic acid dihydrate percolated from the Relite CF resin is percolated again on 100 ml of weak anionic resin, in the ionic form of a free base at the rate of 500 ml/hour. The percolated solution is concentrated to dryness under vacuum, keeping the temperature not above 50° C. 120 ml of ethanol are added and the mixture is refluxed for 1 hour.

The filtered solution is precipitated by adding 3 lt of acetone cooled at 0° C. After a night in the refrigerator, the mixture is filtered and dried at 50° C. under vacuum, giving 50 g of tauroursodesoxycholic acid.

This acid is dissolved in 150 ml of deionized water and precipitated with 3 lt of cool acetone (0° C.). After one night in refrigerator the acid is filtered and dried under vacuum at 50° C., giving 20 g of dihydrated tauroursodesoxycholic acid having a purity of 99.5% and melting point, with decomposition of 143° C.

I claim:

1. A process for the purification of tauroursodesoxycholic acid dihydrate, obtained by the reaction between taurine in the form of an aqueous solution of an alkali metal salt thereof and the mixed anhydride of ursodesoxycholic acid with an alkyl chloroformate, said process comprising the steps of:

passing the product of said reaction serially through a first column of strong cationic exchange resin to obtain a first eluate and passing said first eluate through a second column of weak anionic exchange resin to obtain a second eluate; and purifying the product contained in said second eluate from unreacted taurine and ursodesoxycholic acid.

2. A process according to claim 1, wherein said strong cationic exchange resin is a cationic resin in the form $H^+$.

3. A process according to claim 1, and further comprising monitoring the pH of the eluate of said first column and collecting an eluted fraction having an acid pH.

* * * * *